United States Patent [19]

Amey

[11] 4,351,385
[45] Sep. 28, 1982

[54] TEMPERATURE CONTROL SYSTEM FOR CHROMATOGRAPHS

[75] Inventor: Guy C. Amey, Arkansas City, Kans.

[73] Assignee: The Foxboro Company, Foxboro, Mass.

[21] Appl. No.: 150,534

[22] Filed: May 16, 1980

[51] Int. Cl.³ .................. F25B 29/00; G01N 31/08
[52] U.S. Cl. .................................. 165/61; 165/47; 165/137; 73/23.1; 219/304; 62/457; 126/400
[58] Field of Search .................. 165/61, 64, 10, 137, 165/78; 62/457; 73/23.1; 219/303, 304, 378, 201; 126/400

[56] References Cited

U.S. PATENT DOCUMENTS

| | | | |
|---|---|---|---|
| 3,059,452 | 10/1962 | Griffin | 62/457 |
| 3,290,482 | 12/1966 | Dodd et al. | 219/201 |
| 3,393,729 | 7/1968 | Sauer | 165/61 |
| 3,403,545 | 10/1968 | Carter | 73/23.1 |
| 3,440,397 | 4/1969 | Vesper et al. | 219/209 |
| 3,951,127 | 4/1976 | Watson et al. | 126/206 |
| 4,096,908 | 6/1978 | Lamy | 165/64 |

FOREIGN PATENT DOCUMENTS 315890 10/1971 U.S.S.R. .................... 219/304

Primary Examiner—Albert W. Davis, Jr.
Assistant Examiner—Margaret A. Focarino
Attorney, Agent, or Firm—Andrew T. Karnakis

[57] ABSTRACT

A compact temperature-control unit for use with gas chromatographs. The unit includes a highly insulated enclosure with a removable lid having a gas chromatograph column wound on a thin-walled core fixedly positioned within the enclosure. Provisions are included for inserting a temperature-control module within the cavity formed by the core to achieve temperature control. A variety of different modules can be used to alter the desired control point.

9 Claims, 7 Drawing Figures

ICE AND WATER MIXTURE

SUPERCOOLED MIXTURE

TEMPERATURE CONTROL SYSTEM FOR CHROMATOGRAPHS

FIELD OF THE INVENTION

This invention relates to chromatographic instruments, and more particularly to apparatus adapted for use in controlling the temperature of separation columns commonly employed in such instruments.

BACKGROUND OF THE INVENTION

It has long been recognized that chromatographic instruments are quite temperature sensitive. Retention time and peak heights of the components of the sample undergoing chromatographic analysis are a function of the temperature of the column. Thus when better resolution of component concentration measurements is required, it is desirable to provide chromatographs with temperature-controlling means to hold the equipment temperature within predefined limits.

Although numerous proposals have been offered for achieving this result, in general the separation column(s) have been placed within an enclosed chamber arranged in the form of an oven. The air in the chamber is temperature conditioned and usually elevated above ambient temperature and then forced to flow over the column to exhibit a uniform increased temperature along its entire length. Most often one or more thermostatically controlled electrical resistance heating elements are employed to control the temperature within the oven. Examples of such prior art heating and regulating systems are disclosed in U.S. Pat. Nos. 3,305,000 and 3,309,504.

These prior art systems are undesirable for use in certain applications due in part to their bulkiness which severely hampers their use as portable (i.e., man-carried) field-operable instruments. However, the disadvantages of the prior art are perhaps most accented because they involve active means to bring about the requisite temperature control, that is in the majority of applications electrical energy, in the form of current-generated electrical resistance heaters, is introduced. The required electrical power is not normally available with portable equipment because of its size, weight and service life requirements. In addition, the heaters, controllers, and other conventional equipment are not compatible with intrinsically safe equipment design criteria which is a desirable and often mandatory prerequisite for portable chromatographic equipment.

SUMMARY OF THE INVENTION

The present invention relates to an apparatus capable of achieving temperature control over a chromatographic column under field of conditions by totally passive means, that is influencing an a predetermined manner and for a fixed period of time the temperature of the column without the need for an externally supplied source of energy to bring about the requisite heat transfer.

In accordance with a preferred embodiment of the invention to be subsequently described in detail, there is provided a compact, passive temperature-control unit for use with gas chromatographs. The control unit includes a urethane foam-insulated container having a gas chromatograph column wound around a thin-walled metal core which forms an inner cavity, with the column and metal core being foamed in place within the container. The ends of the column extend outside the container and are connected to the rest of the chromatograph and thus serve to transport carrier gas and sample to and from the column. Temperature control is effectuated by removing the container cover and inserting a tight-fitting temperature-control module into the cavity. The module represents a self-contained energy unit either in the form of a bottle containing the temperature-control media (e.g., a mixture of water and ice) or a solid mass of similar shape that has been preheated, or alternatively precooled, to a desired temperature. Because the overall unit is so highly insulated and because the temperature-control module is in direct heat transfer relationship with the core, desired column temperatures can be attained for a considerable length of time.

Since a variety of temperature-control modules can be used with the unit, the temperature range can accordingly be varied to permit analysis of light compounds at low temperature (0° C.) as well as analysis of heavier compounds at increased temperatures (100° C.) with the same column. Moreover, changeover to different temperatures is rapidly and conveniently accomplished by simply inserting another module into the core cavity, thereby further enhancing the flexibility of the instrument.

Furthermore, because the modules are self-contained energy packs, no external source of energy (especially electrical energy) is required to activate the temperature-control unit. Hence, the unit is intrinsically safe and may be approved for use in Class 1, Division 1 (all groups) environments as defined by Article 500 of the National Electrical Code and also in those hazardous locations determined by equivalent foreign certifying agencies.

BRIEF DESCRIPTION OF THE DRAWINGS

Other aspects, features, and advantages of the present invention will become apparent in light of the following description of the preferred embodiment read in conjunction with the associated drawings.

DESCRIPTION OF THE PREFERRED EMBODIMENT

Figure 1:
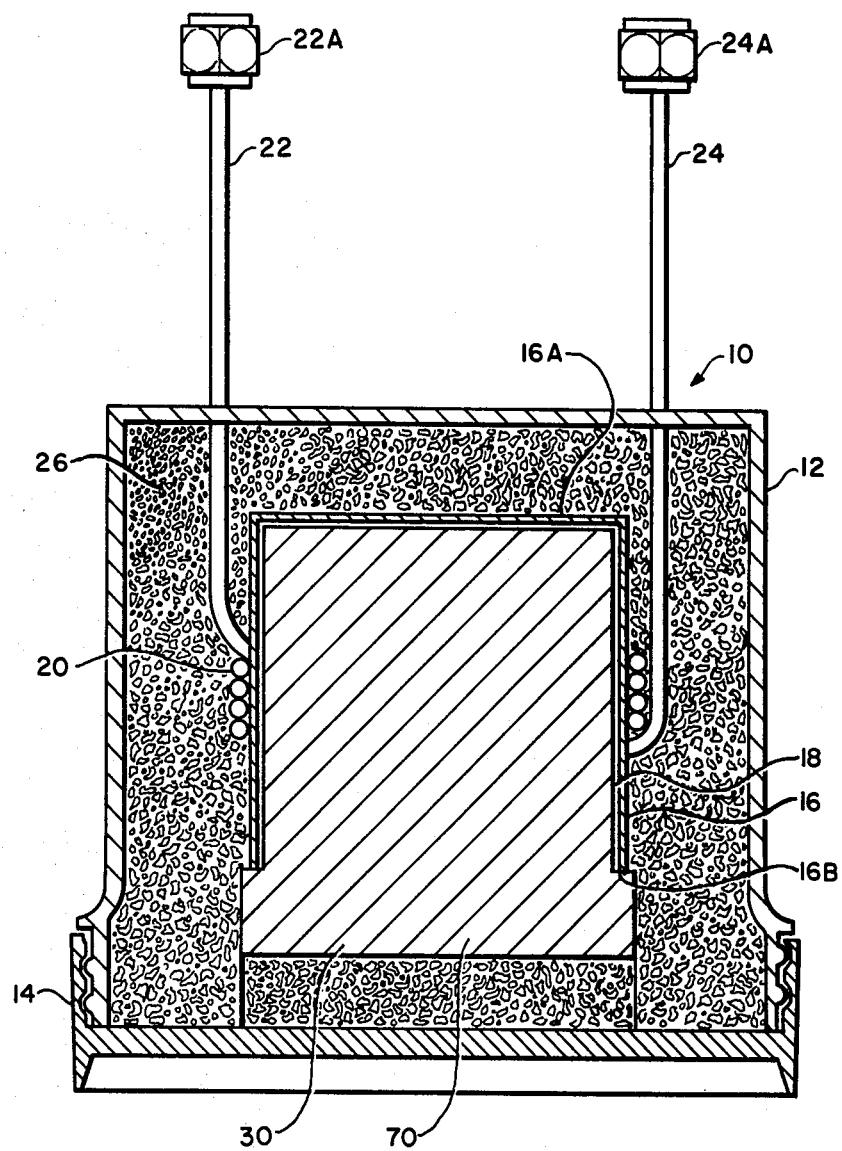
FIG. 1 is a cross-sectional view of the temperature-control unit of the preferred embodiment showing one temperature-control module inserted therein.

Referring now to FIG. 1, there is shown a temperature-control unit 10 constructed in accordance with the present invention for use with a gas chromatograph and including a cylindrical polypropylene container 12. The container is very compact, measuring 4.5 inches in diameter by 4.0 inches high. At one end of the container, a removable screw-on lid 14 permits ready access to the interior of the container.

Positioned approximately at the diametric center of the container 12 is a thin-walled aluminum tubular liner 16 having a closed end 16A and an open end 16B defining an inner cavity 18. A gas chromatograph column 20 is wound around the liner with the respective ends 22, 24 extending outside the top of the container for connection via a pair of couplings 22A, 24A to other operating units of the chromatograph (e.g., carrier supply, sample insert, detector, etc.). Although packing material is only located in the portion of the column wrapped around the liner, extending the column in this manner eliminates the need for internal column connections which can break or leak and thereby enhances the flexibility and portability of the temperature-control unit.

The liner 16 and column 20 are fixedly held in position within the container 12 by a polyurethane foam 26 which completely fills the void between the walls of the liner and the container and also surrounds the column and that portion of its extended ends located within the container. In this manner, complete insulation is provided around the liner except at the open end 16B where the lid 14 is attached. However, the lid itself contains foaming material and thus the entire container presents a highly insulated enclosure.

Temperature control is achieved by inserting into the inner cavity 18 a temperature-control module 30. The shape of the module closely matches that of the cavity such that with the module in position there is a snug fit with the walls of the cavity, and the module is thus in direct heat transfer relationship with the liner 16 and correspondingly the column 20 itself. This construction provides excellent heat transfer within the container, which at the same time effectively minimizes outward heat transfer, and results in rapid initial temperature stabilization and minimum temperature gradient between the temperature-control module and the column.

Figure 7:
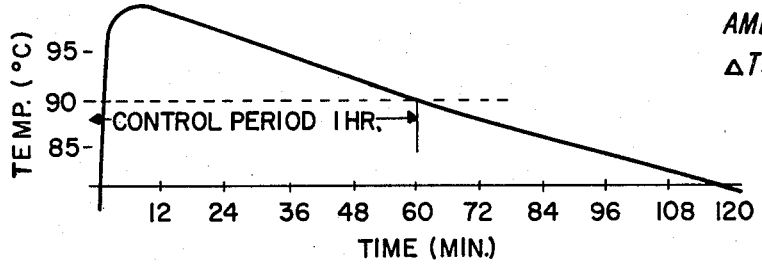
FIG. 7 is a graph, drawn to a different time scale from that of the graphs of FIGS. 5 and 6, of temperature vs. time for a fixed ambient temperature indicating test-performance results of the temperature-control unit of the present invention when operating with the temperature-control module of FIG. 1.

For illustrative purposes only, FIG. 1 shows a solid mass module 70 in the shape of a bottle inserted into the cavity. This module can be either preheated or precooled to hold the temperature of the column 20 above or below a fixed temperature for a certain period of time. FIG. 7 demonstrates that a mass of aluminum heated to 100° C. is capable of holding column temperature above 90° C. for one hour when the temperature-control unit is exposed to an ambient temperature of 25° C.

Figure 2:
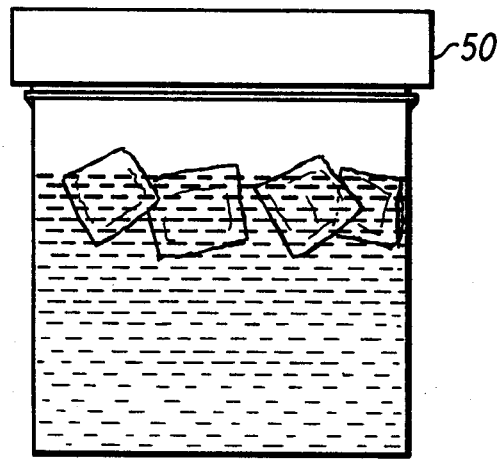
FIG. 2 is a cross-sectional view of another temperature-control module.
Figure 3:
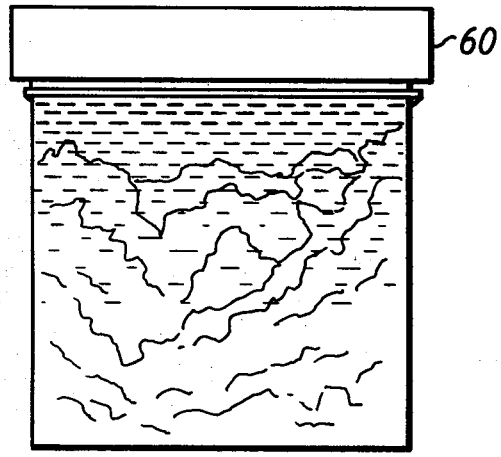
FIG. 3 is a cross-sectional view of another temperature-control module.
Figure 5:
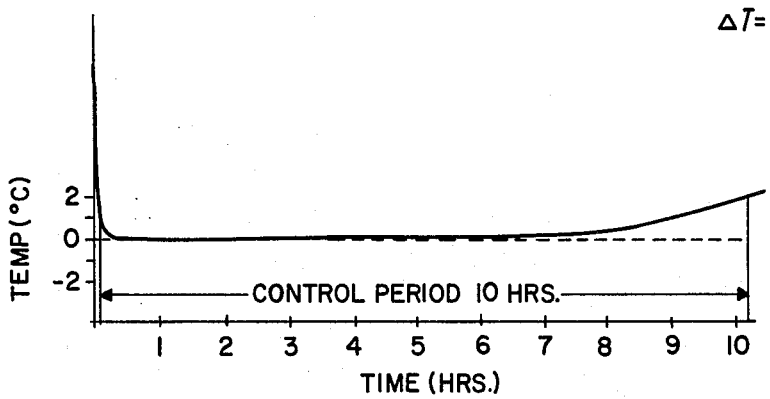
FIG. 5 is a graph of temperature vs. time for a fixed ambient temperature indicating test-performance results of the temperature-control unit of the present invention when operating with the temperature-control module of FIG. 2.

However in the most common situation, the module desired will be a six fluid ounce bottle (see FIGS. 2 and 3) that contains a temperature-control media, i.e., a mixture of materials capable of providing isothermal temperature control for prolonged periods of time while the media is undergoing a phase change. FIG. 2 represents a temperature-control module 50 filled with a mixture of ice and water which, as is well known, provides extremely stable isothermal temperature control at 0° C. When inserted into the temperature-control unit 10, this module produces a negative heat transfer effect by cooling the column 20 and after an initial brief stabilization period holding its temperature at 0° C. for as long as the media contains ice. FIG. 5 illustrates that at an ambient temperature of 27° C. the module 50 when positioned into the temperature-control apparatus of the present invention maintains a column temperature of 0° C. for 8 hours and only deviates from that control temperature by 1° C. after an additional 2 hours.

Figure 6:
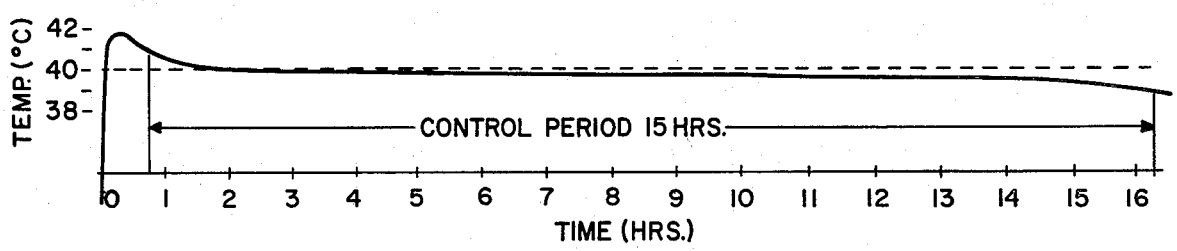
FIG. 6 is a graph, drawn to the same time scale as the graph of FIG. 5, of temperature vs. time for a fixed ambient temperature indicating test-performance results of the temperature-control unit of the present invention when operating with the temperature-control module of FIG. 3.

It is sometimes desirable to heat the column 20 and keep its temperature at a fixed elevated value so as to facilitate analysis of heavier compounds. For these purposes, the temperature-control module 60 of FIG. 3 can be used to provide positive heat transfer. This module contains a liquid solution of a supercooled chemical, sodium thiosulfate pentahydrate, ethylene glycol, and water that is maintained below the solution's melting point (approximately 40° C.). Just prior to inserting the module, the solution is seeded with sodium borate pentahydrate which crystallizes the sodium thiosulfate solution at the substantially constant temperature of its melting point (i.e., 40° C.). Further details concerning the use of supercooled chemicals to produce constant temperature effects may be found in U.S. Pat. No. 3,951,127. In FIG. 6 it can be seen that the column temperature can be maintained nominally (i.e., $\pm 1°$ C.) at 40° C. for about 16 hours at an ambient temperature of 25° C. when the module 60 is employed in the system.

It is apparent that the temperature-control modules may contain any number of different chemicals and materials and in varying portions to develop specific temperature control points within a wide range of values. Furthermore, solid masses of different materials with different heat transfer characteristics, such as brass, can be employed and need only be suitably temperature conditioned in a water bath or temperature chamber of desired temperature.

Figure 4:
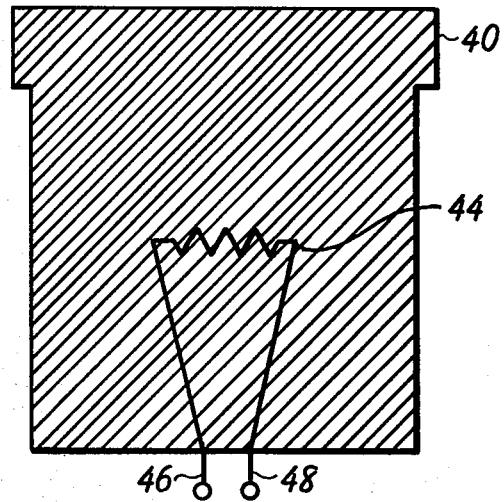
FIG. 4 is a cross-sectional view of still another temperature-control module.

FIG. 4 shows a variation to the preferred configurations discussed above, one that may find desirable application in a laboratory as opposed to field environment. The temperature-control module 40 is an aluminum mass similar to the module 30 shown in FIG. 1; however, embedded in the module 40 is an electrical resistance heating element 44 with corresponding connecting wires 46, 48 leading to a power source (not shown). The module 40 is particularly suitable in cleaning and conditioning new or used columns, and because of the overall arrangement of the temperature-control unit 10, especially its high insulation qualities, the columns can be cleaned while on the shelf instead of in specially formulated ovens using nitrogen purge and the like. Of course, the module 40 can also be used to provide temperature control as explained above if the application warrants. This electrically controlled module can also be used for temperature programming of the column.

The embodiments described above demonstrate the performance advantages and flexibility of the present invention. The use of variable-temperature control modules means that a single column or column set can be utilized for the analysis of a wide range of compounds. For example, a single temperature-control unit 10 could be used for the analysis of relatively light $C_2$-$C_3$ compounds when a 0° C. module is inserted. Then, without making any other changes to the apparatus, a 40° C. module could be readily inserted by simply unscrewing the lid 14 and changing modules to allow analysis of heavier compounds such as styrene. Also, importantly in most applications, temperature control can be achieved by passive means through a self-contained energy source and thus is intrinsically safe.

Although the invention has been described with reference to particular embodiments, these examples are solely for illustrative purposes and thus are not to be construed as limiting because modifications and variations will become apparent to those of skill in the art.

What is claimed is:

1. A field-operable, portable chromatographic instrument, comprising, in combination, a container with a removable cover to permit ready access to the interior thereof;

wall means within said container defining an interior cavity having an insert opening at one end thereof, said wall means being capable of high rates of heat transfer;

a chromatographic column wound around said wall means and being in direct heat transfer relationship therewith;

heat insulation means surrounding said column to substantially minimize outward heat transfer away from said container;

a temperature-control module adapted to be inserted within said interior cavity, the shape of said module matching that of said cavity such that when inserted therein said module is in direct heat transfer relationship with said wall means and hencewith said column, said module including means for receiving and storing thermal energy from an external source, said module being isolated from said external source when inserted in said cavity, said module further including means for transferring stored thermal energy received from said external source between said storing means and said column so as to maintain the temperature of said column at a predetermined value for a period of time long enough to permit chromatographic analysis independent of the transfer to said storing means of more thermal energy from said external source, whereby;

said module is a self-contained source of energy for providing effective temperature control over said column.

2. Apparatus as claimed in claim 1 wherein said module is a solid body of material having predetermined heat transfer characteristics, said body being capable of storing thermal energy so as to produce positive or negative heat transfer effects between said body and said wall means to control the temperature of said column at a desired value.

3. Apparatus as claimed in claim 2 wherein said body is aluminum.

4. Apparatus as claimed in claim 1 wherein said module is a closed receptacle containing temperature-control media.

5. Apparatus as claimed in claim 4 wherein said media is a mixture of ice and water producing an isothermal temperature of 0° C.

6. Apparatus as claimed in claim 4 wherein said media is a supercooled chemical seeded with a crystallizing agent.

7. Apparatus as claimed in claim 6 wherein said supercooled chemical is a solution of sodium thiosulfate pentahydrate, ethylene glycol and water and said crystallizing agent is sodium borate pentahydrate, whereby said module produces a constant temperature of 40° C.

8. Apparatus as claimed in claim 1 wherein said wall means defines a generally circular cylindrical cavity.

9. Apparatus as claimed in claim 8 wherein said wall means is a thin-walled aluminum tubular liner having a closed end opposite said insert opening.

* * * * *